United States Patent
Nett et al.

(10) Patent No.: US 9,858,688 B2
(45) Date of Patent: Jan. 2, 2018

(54) METHODS AND SYSTEMS FOR COMPUTED TOMOGRAPHY MOTION COMPENSATION

(71) Applicant: General Electric Company, Schenectady, NY (US)

(72) Inventors: Brian Edward Nett, Brookfield, WI (US); Caroline Elise Seng, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 91 days.

(21) Appl. No.: 14/755,870

(22) Filed: Jun. 30, 2015

(65) Prior Publication Data
US 2017/0004636 A1     Jan. 5, 2017

(51) Int. Cl.
*G06K 9/00* (2006.01)
*G06T 11/00* (2006.01)
*A61B 6/00* (2006.01)
*A61B 6/03* (2006.01)

(52) U.S. Cl.
CPC ............ *G06T 11/005* (2013.01); *A61B 6/032* (2013.01); *A61B 6/5205* (2013.01); *A61B 6/5264* (2013.01); *G06T 2210/41* (2013.01)

(58) Field of Classification Search
CPC ....... A61B 6/032; A61B 6/463; A61B 6/5264; G06T 11/005; G06T 2207/10081; G06T 7/20; G06T 7/2053; G06T 2207/20224; G06T 2210/41
See application file for complete search history.

(56) References Cited

U.S. PATENT DOCUMENTS

| | | | |
|---|---|---|---|
| 4,994,965 A | 2/1991 | Crawford et al. |
| 5,412,562 A | 5/1995 | Nambu et al. |
| 6,236,705 B1 | 5/2001 | Stergiopoulos et al. |
| 6,385,286 B1 | 5/2002 | Fitchard et al. |
| 6,393,090 B1 | 5/2002 | Hsieh et al. |
| 6,421,552 B1 | 7/2002 | Hsieh |
| 6,535,570 B2 | 3/2003 | Stergiopoulos et al. |
| 6,674,836 B2 | 1/2004 | Harada et al. |
| 7,142,637 B2 | 11/2006 | Nagai |
| 7,292,721 B2 | 11/2007 | Arnold |

(Continued)

OTHER PUBLICATIONS

Bresler, Y. et al., "Optimal Interpolation in Helical Scan 3D Computerized Tomography," 1989 International Conference on Acoustics, Speech, and Signal Processing (ICASSP-89), May 23, 1989, Glasgow, Scotland, 4 pages.

(Continued)

*Primary Examiner* — Amara Abdi
(74) *Attorney, Agent, or Firm* — McCoy Russell LLP

(57) ABSTRACT

Methods and systems are provided for motion compensation in computed tomography imaging. In one embodiment, a method comprises reconstructing at least two images from projection data, calculating a motion metric based on the at least two images, selecting a view-weighting function based on the motion metric, and generating a display from the projection data based on the selected view-weighting function. In this way, an image can be reconstructed with the selected view-weighting function which down-weights slices in the image containing motion artifacts. As a result, the image quality of the reconstructed image may be improved with computational efficiency.

20 Claims, 6 Drawing Sheets

(56) References Cited

U.S. PATENT DOCUMENTS

| | | | |
|---|---|---|---|
| 7,471,765 B2 | 12/2008 | Jaffray et al. | |
| 8,224,056 B2 | 7/2012 | Pack et al. | |
| 8,270,561 B2 | 9/2012 | Zamyatin et al. | |
| 8,284,892 B2* | 10/2012 | Pack | A61B 6/032 378/210 |
| 2003/0095695 A1 | 5/2003 | Arnold | |
| 2012/0093281 A1 | 4/2012 | Zamyatin et al. | |
| 2014/0133622 A1* | 5/2014 | Yin | A61B 6/032 378/8 |
| 2014/0254905 A1* | 9/2014 | Pack | G06T 11/006 382/131 |
| 2015/0253409 A1* | 9/2015 | Feiweier | G01R 33/307 324/307 |

OTHER PUBLICATIONS

Ho, H. et al., "Fast and Accurate Stratification of Tomographic Scans for Motion Artifacts," Third International Conference on Image Formation in X-Ray Computed Tomography, Jun. 22, 2014, Salt Lake City, Utah, 4 pages.

Wang, G. et al., "Preliminary Study on Helical CT Algorithms for Patient Motion Estimation and Compensation," IEEE Transactions on Medical Imaging, vol. 14, No. 2, Jun. 1995, 7 pages.

Ritchie, C. et al., "Correction of Computed Tomography Motion Artifacts Using Pixel-Specific Back-Projection," IEEE Transactions on Medial Imaging, vol. 15, No. 3, Jun. 1996, 10 pages.

Wilson, M. et al., "Automated Detection of Microcalcifications in Mammograms through Application of Image Pixel Remapping and Statistical Filter," 11th IEEE Symposium on Computer-Based Medical Systems, Jun. 12, 1998, 5 pages.

Jaffray, D. et al., "Cone-Beam Computed Tomography with a Flat-Panel Imager: Initial Performance Characterization," Medical Physics, vol. 27, No. 6, Jun. 2000, 13 pages.

Manzke, R. et al., "Automatic Phase Determination for Retrospectively Gated Cardiac CT," Medical Physics, vol. 31, No. 12, Dec. 2004, 18 pages.

* cited by examiner

METHODS AND SYSTEMS FOR COMPUTED TOMOGRAPHY MOTION COMPENSATION

FIELD

Embodiments of the subject matter disclosed herein relate to non-invasive diagnostic imaging, and more particularly, to computed tomography (CT) systems and methods for improving image quality.

BACKGROUND

Non-invasive imaging technologies allow images of the internal structures of a patient or object to be obtained without performing an invasive procedure on the patient or object. In particular, technologies such as computed tomography (CT) use various physical principals, such as the differential transmission of x-rays through the target volume, to acquire image data and to construct tomographic images (e.g., three-dimensional representations of the interior of the human body or of other imaged structures).

However, image reconstruction algorithms generally assume that the subject of the scan is stationary throughout the data acquisition. Thus, if the patient or object moves during data acquisition, motion artifacts may arise in the tomographic images, or image reconstructions. Such artifacts can lead to confusion for a physician or patient reviewing the reconstructed image.

Known approaches to motion correction typically determine a motion path and attempt to compensate for motion during reconstruction or post-reconstruction based on the motion path. However, such approaches come with the cost of significant algorithmic complexity and computational expense, as well as substantially increased reconstruction time. It may therefore be desirable to develop an efficient technique to improve image quality of acquired CT images by reducing motion artifacts.

BRIEF DESCRIPTION

In one embodiment, a method comprises reconstructing at least two images from projection data, calculating a motion metric based on the at least two images, selecting a view-weighting function based on the motion metric, and generating a display from the projection data based on the selected view-weighting function. In this way, an image can be reconstructed with the selected view-weighting function which down-weights slices in the image containing motion artifacts. As a result, the image quality of the reconstructed image may be improved with computational efficiency.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 5:
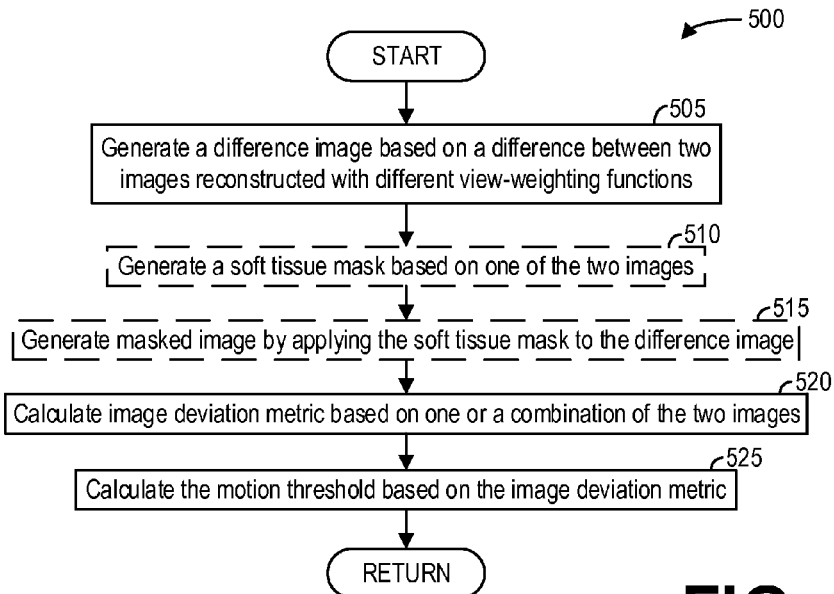
FIG. 5 shows a high-level flow chart illustrating an example method for calculating a motion threshold.
Figure 6:
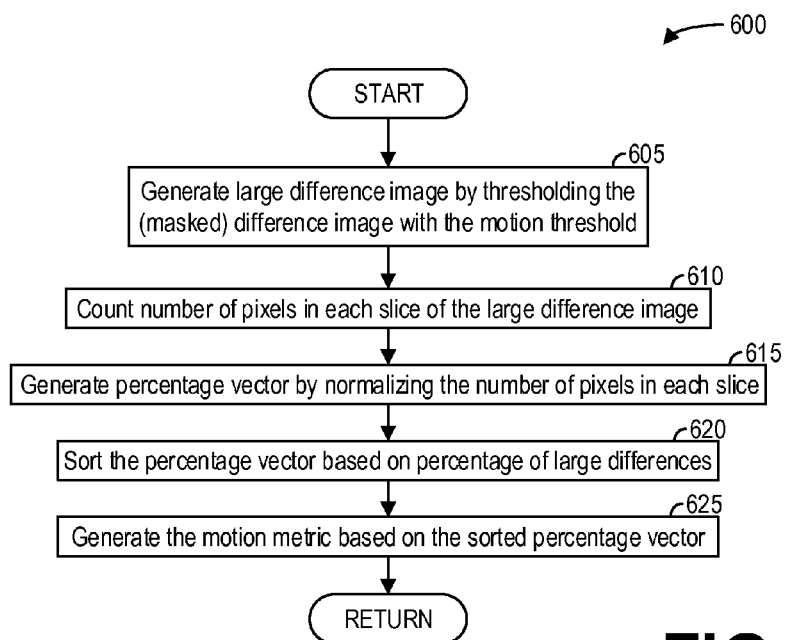
FIG. 6 shows a high-level flow chart illustrating an example method for calculating a motion metric.

The following description relates to various embodiments of medical imaging systems. In particular, methods and systems are provided for motion compensation with computed tomography imaging. An example of a computed tomography (CT) imaging system that may be used to acquire images processed in accordance with the present techniques is provided in FIGS. 1 and 2. A general method for reconstructing an image based on a motion estimate, such as the method shown in FIG. 3, may include reconstructing intermediate images and calculating a motion estimate based on the intermediate images. A more specific method for reconstructing an image with reduced motion artifacts, such as the method shown in FIG. 4, may include reconstructing an un-weighted image and a weighted image, and estimating motion based on the un-weighted image and the weighted image. One method for estimating motion includes calculating a motion threshold, as shown in FIG. 5. Another method for estimating motion includes calculating a motion metric, as shown in FIG. 6, which may utilize the motion threshold to quantify an amount of motion that occurs during a scan. The intermediate images may be reconstructed according to different view-weighting functions, examples of which are shown in FIGS. 7-10.

Though a CT system is described by way of example, it should be understood that the present techniques may also be useful when applied to images acquired using other imaging modalities, such as tomosynthesis, MRI, C-arm angiography, and so forth. The present discussion of a CT imaging modality is provided merely as an example of one suitable imaging modality.

Figure 1:
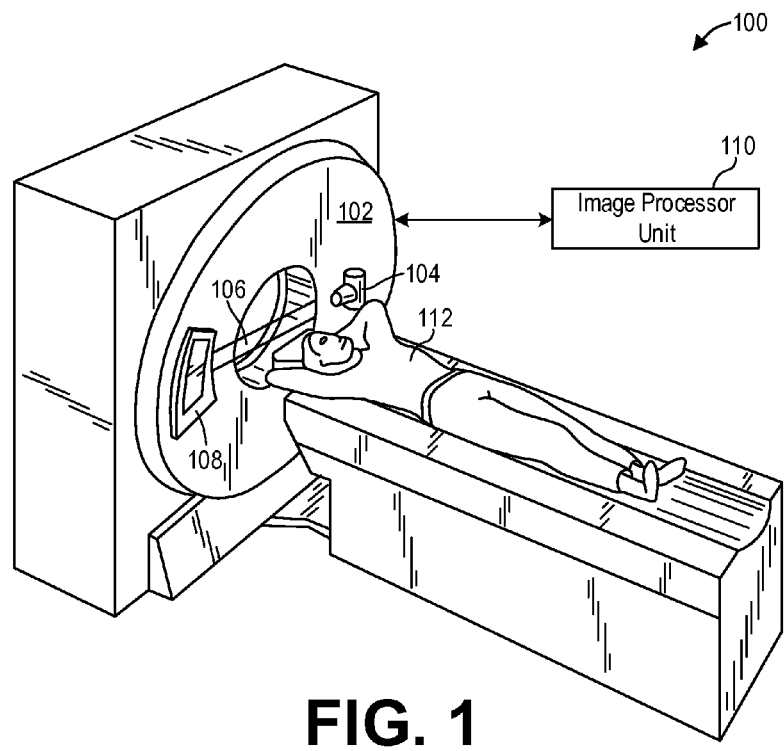
FIG. 1 shows a pictorial view of an imaging system.

FIG. 1 illustrates an exemplary CT system 100 configured to allow fast and iterative image reconstruction. Particularly, the CT system 100 is configured to image a subject such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray radiation source 104 configured to project a beam of x-ray radiation 106 for use in imaging the patient. Specifically, the radiation source 104 is configured to project the x-rays 106 towards a detector array 108 positioned on the opposite side of the gantry 102. Although FIG. 1 depicts only a single radiation source 104, in certain embodiments, multiple radiation sources may be employed to project a plurality of x-rays 106 for acquiring projection data corresponding to the patient at different energy levels.

In certain embodiments, the CT system 100 further includes an image processing unit 110 configured to reconstruct images of a target volume of the patient using an iterative or analytic image reconstruction method. For example, the image processing unit 110 may use an analytic image reconstruction approach such as filtered backprojection (FBP) to reconstruct images of a target volume of the patient. As another example, the image processing unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the patient.

In some known CT imaging system configurations, a radiation source projects a fan-shaped beam which is collimated to lie within an X-Y plane of a Cartesian coordinate system and generally referred to as an "imaging plane." The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In some CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view." A "scan" of the object includes a set of views made at different gantry angles, or view angles, during one revolution of the radiation source and detector. It is contemplated that the benefits of the methods described herein, wherein intermediate images are reconstructed from the same projection data with different view-weighting functions, accrue to medical imaging modalities other than CT, so as used herein the term view is not limited to the use as described above with respect to projection data from one gantry angle. The term "view" is used to mean one data acquisition whenever there are multiple data acquisitions from different angles, whether from a CT, PET, or SPECT acquisition, and/or any other modality including modalities yet to be developed as well as combinations thereof in fused embodiments.

In an axial scan, the projection data is processed to reconstruct an image that corresponds to a two-dimensional slice taken through the object. One method for reconstructing an image from a set of projection data is referred to in the art as the filtered backprojection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

Figure 2:
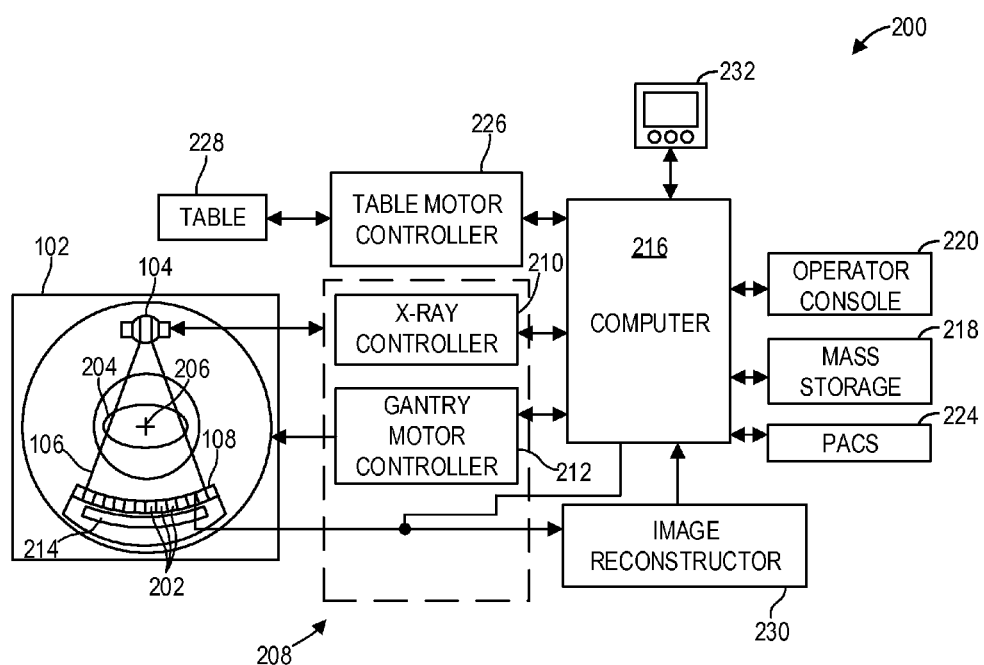
FIG. 2 shows a block schematic diagram of an exemplary imaging system.

FIG. 2 illustrates an exemplary imaging system 200 similar to the CT system 100 of FIG. 1. In accordance with aspects of the present disclosure, the system 200 is configured to reconstruct images with reduced motion artifacts. In one embodiment, the system 200 includes the detector array 108 (see FIG. 1). The detector array 108 further includes a plurality of detector elements 202 that together sense the x-ray beams 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

In one embodiment, the system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computing device 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage device.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the system 200, for example, for inputting or outputting system parameters, requesting examinations, and/or viewing images. Further, in certain embodiments, the system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the system 200 either includes, or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a motorized table 228. Particularly, the table motor controller 226 moves the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the system 200 and instead the computing device 216 may perform one or more functions of the image reconstructor 230. Moreover, the image reconstructor 230 may be located locally or remotely, and may be operatively connected to the system 100 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230.

The various methods and processes described further herein may be stored as executable instructions in non-transitory memory on a computing device in system 200. In one embodiment, image reconstructor 230 may include such instructions in non-transitory memory, and may apply the methods described herein to reconstruct an image from scanning data. In another embodiment, computing device 216 may include the instructions in non-transitory memory, and may apply the methods described herein, at least in part, to a reconstructed image after receiving the reconstructed image from image reconstructor 230. In yet another embodiment, the methods and processes described herein may be distributed across image reconstructor 230 and computing device 216.

In one embodiment, the display 232 allows the operator to evaluate the imaged anatomy. The display 232 may also allow the operator to select a volume of interest (VOI) and/or request patient information, for example, via graphical user interface (GUI) for a subsequent scan or processing.

Image reconstruction algorithms generally assume that the subject of the scan is stationary throughout the acquisition. The image reconstruction function is a function of x-ray attenuation in three-dimensional space. When motion occurs during the acquisition, the stationary assumption is violated and motion artifacts appear in the reconstructed images. The image function becomes a function of time as well. A method for correcting for such motion includes applying a view weighting to the acquired projection data such that conjugate rays where motion has occurred are down-weighted, resulting in fewer motion artifacts. The methods described herein below comprise data-driven methods to determine an effective view-weighting function based on the motion which occurred during the acquisition, without otherwise sacrificing image quality. The methods described herein dynamically detect the severity of clinically-significant motion artifacts in image space at an intermediate point in reconstruction, and modify the effective view-weighting function based on the severity of motion determined from the data. In particular, the technique described herein inputs multiple images to determine the effective view weighting.

Figure 3:
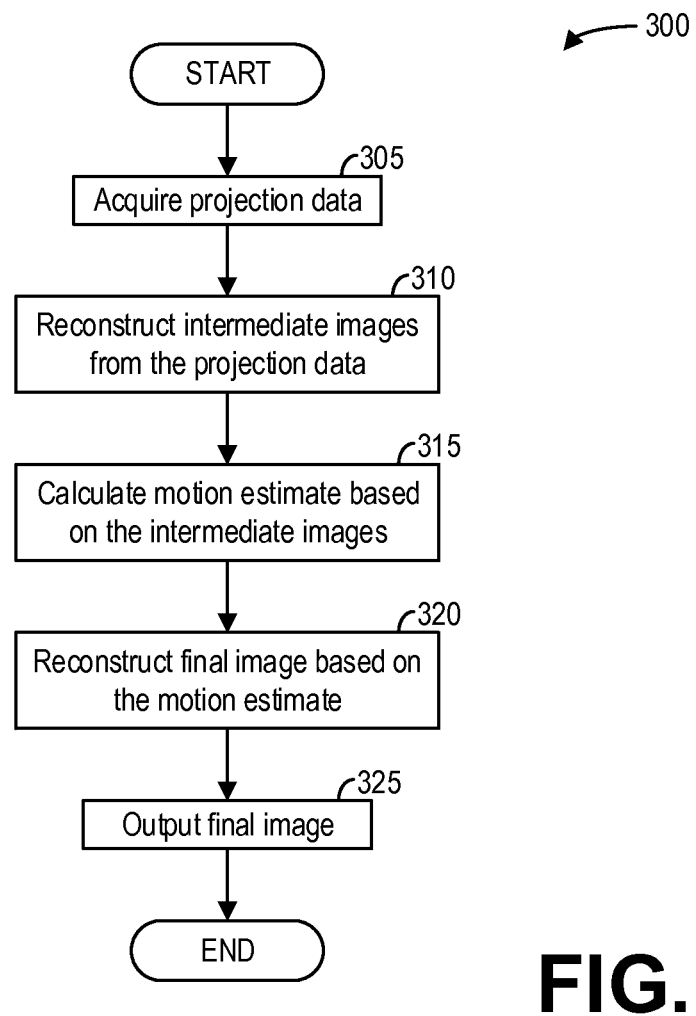
FIG. 3 shows a high-level flow chart illustrating an example method for reconstructing an image based on a motion estimate.

FIG. 3 shows a high-level flow chart illustrating an example method 300 for reconstructing an image according to an embodiment. In particular, method 300 relates to estimating motion in one or more intermediate images, and reconstructing a final image based on the motion estimate. Method 300 may be carried out by the components and systems depicted in FIGS. 1 and 2, however it should be understood that the method may be implemented on other components and systems not depicted without departing from the scope of the present disclosure.

Method 300 begins at 305. At 305, method 300 includes acquiring projection data. Projection data may be acquired over a full scan. Alternatively, projection data may be acquired over less than a full scan of data, thereby minimizing exposure of the object to radiation administered during the scan.

At 310, method 300 includes reconstructing intermediate images from the acquired projection data. In some examples, the intermediate images may be reconstructed using analytic reconstruction methods such as filtered backprojection. In other examples, the intermediate images may be reconstructed using iterative reconstruction methods.

Although the intermediate images are reconstructed from the same data, the reconstructions differ such that any motion during the scan may be detected by comparing the intermediate images. For example, the intermediate images may be reconstructed with different temporal widths, center views, view-weighting functions, and so on. As an example, the intermediate images may include an un-weighted full-scan image and at least one weighted half-scan image, wherein the images have a same center view. In this way, motion may be estimated by considering the difference between the un-weighted full scan image and the at least one weighted half-scan image. In other examples, the intermediate images may be reconstructed with different center views and a same temporal width. In yet other examples, the intermediate images may be reconstructed with different center views and different temporal widths.

After reconstructing the intermediate images, method 300 continues to 315. At 315, method 300 includes calculating a motion estimate based on the intermediate images. Calculating the motion estimate may include calculating an amount of noise caused by motion in each slice of an image. Example methods for estimating motion in the intermediate images is described further herein and with regard to FIGS. 4-6.

At 320, method 300 includes reconstructing a final image based on the motion estimate. In some examples, the motion estimate is used to generate an optimal view-weighting function which down-weights slices containing motion artifacts. The final image may then be reconstructed with the optimal view-weighting function.

In other examples, the motion estimate may indicate that at least one of the view-weighting functions used to reconstruct the intermediate images effectively reduces motion artifacts. In such examples, since one of the intermediate images was reconstructed with the effective view-weighting function at 310, additional reconstruction is redundant and the intermediate image reconstructed with the effective view-weighting function is selected as the final image.

At 325, method 300 includes outputting the final image. Outputting the final image may comprise transmitting the final image to a display device, such as display device 232 in FIG. 2, for display to a user of the imaging system. Additionally or alternatively, the final image may be output to non-transitory memory for subsequent processing, retrieval, and/or display. Alternatively, the final image may be output to another computing module for additional artifact correction and processing. Method 300 may then end.

Thus, a method for reconstructing an image includes reconstructing intermediate images from projection data, estimating motion based on the intermediate images, and reconstructing a final image based on the motion estimation. In this way, the image quality of reconstructed images can be improved, as the amount of motion artifacts may be reduced.

Figure 4:
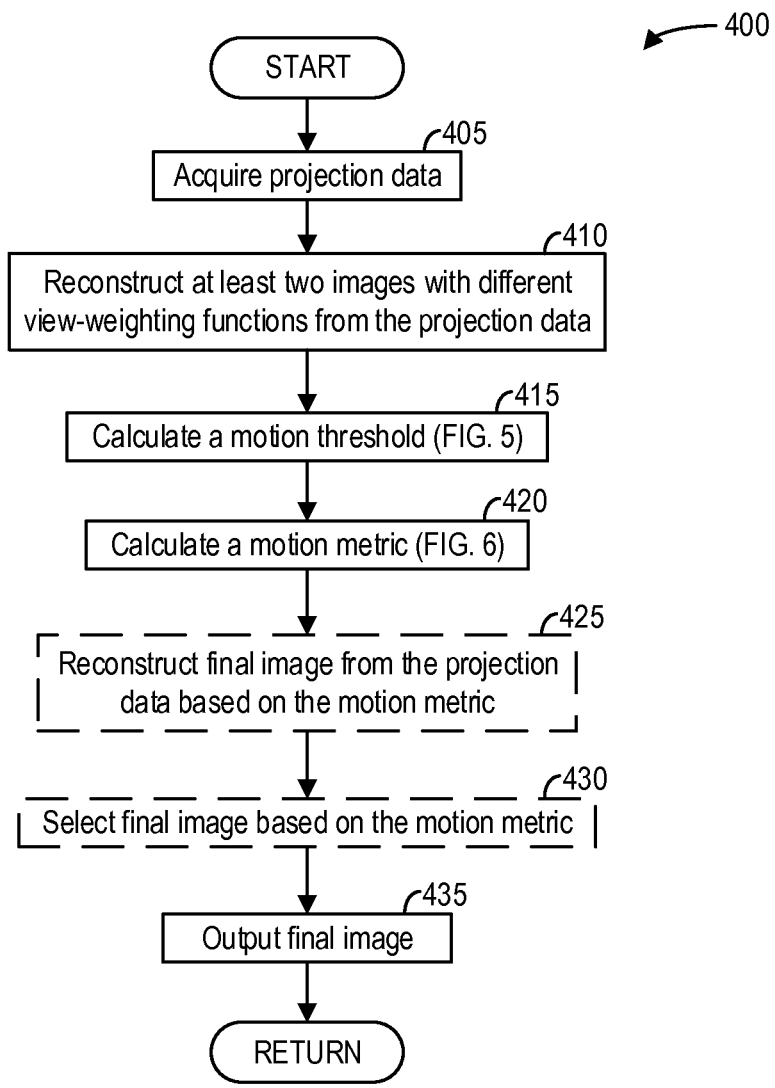
FIG. 4 shows a high-level flow chart illustrating an example method for reconstructing an image based on a motion metric.

FIG. 4 shows a high-level flow chart illustrating an example method 400 for reconstructing an image according to an embodiment. In particular, method 400 relates to reconstructing intermediate images using different view-weighting functions to estimate motion within the intermediate images. An image with reduced motion artifacts may be reconstructed or selected for output based on the motion estimation. Method 400 will be described with reference to the components and systems depicted in FIGS. 1 and 2, however it should be understood that the method may be applied to different components and systems without departing from the scope of the disclosure.

Method 400 begins at 405. At 405, method 400 includes acquiring projection data. Projection data may be acquired over a full scan. However, in some examples, projection data may be acquired over less than a full scan. Furthermore, the projection data may be acquired using an axial scan. However, it should be appreciated that in some examples, projection data may be acquired using a helical scan.

At 410, method 400 includes reconstructing at least two images with different view-weighting functions from the projection data. As a non-limiting example, reconstructing at least two images with different view-weighting functions may comprise reconstructing an un-weighted image and at least one weighted image from the projection data. In one example, the un-weighted image comprises a full-scan image while the at least one weighted image comprises a half-scan image. In some examples, the at least one weighted image comprises a plurality of weighted images, wherein each of the plurality of weighted images is reconstructed with a different view-weighting function. Example view-weighting functions are described further herein with regard to FIGS. 7-10.

At 415, method 400 includes calculating a motion threshold. A motion threshold may be calculated for each image with respect to another image. As described further herein with regard to FIG. 5, the motion threshold may be calculated based on a difference between the images, and may be used to detect motion occurring within or between the images. As an example, in examples including a plurality of weighted images and one un-weighted (i.e., full scan) image, a motion threshold may be calculated for each of the plurality of weighted images with respect to the un-weighted image.

At 420, method 400 includes calculating a motion metric. The motion metric, comprising a numerical value which quantitatively describes the severity of motion in an image, is calculated using the motion threshold. Thus, in examples including a plurality of weighted images and an un-weighted image, a motion metric may be calculated for each of the plurality of weighted images. A method for calculating a motion metric is described further herein and with regard to FIG. 6.

After calculating the motion metric, method 400 may proceed to one of two actions, 425 or 430. In some examples, method 400 proceeds to 425 and then skips 430. Similarly, in other examples, method 400 skips 425 and proceeds to 425. Thus the actions 425 and 430 are mutually exclusive.

At 425, method 400 may optionally include reconstructing a final image from the projection data based on the motion metric. Specifically, a new view-weighting function may be generated based on the motion metric, and a final image may be reconstructed using the new view-weighting function. The new view-weighting function may be generated such that, for an image reconstructed with the new view-weighting function, slices containing significant motion are down-weighted while slices without motion are up-weighted. The final image is reconstructed from the same projection data as the intermediate images reconstructed at 410.

If a final image is reconstructed at 425, method 400 bypasses 430 and proceed directly to 435. However, if a final image is not reconstructed at 425, then method 400 proceeds to 430. At 430, method 400 may optionally include selecting a final image based on the motion metric. For example, considering an example wherein the at least two images comprise a half-scan image and a full-scan image, if the motion metric characterizing the two images is above a threshold, then significant motion is present and the half-scan image is selected as the final image; if the motion metric is below the threshold, then the full-scan image is selected as the final image. Similarly, considering a plurality of view-weighted images and an un-weighted (i.e., full scan) image, if one or more of the motion metrics for the plurality of weighted images is below the threshold, then significant motion has not occurred and the un-weighted image is selected as the final image; if all of the motion metrics are above the threshold, then the weighted image with the largest motion metric is selected as the final image.

At 435, method 400 includes outputting the final image. Outputting the final image may comprise transmitting the final image to a display device, such as display device 232 in FIG. 2, for display to a user of the imaging system. Thus method 400 may include generating a display from the projection data with a view-weighting function selected or generated based on the motion metric. Additionally or alternatively, the final image may be output to non-transitory memory for subsequent processing, retrieval, and/or display. Alternatively, the final image or the selected view-weighting function may be output to another computing module for additional artifact correction and processing. Method 400 then ends.

Thus, a method for reducing motion artifacts includes reconstructing at least two images from acquired projection data with different view-weighting functions, calculating a motion threshold based on a difference of the at least two images, calculating a motion metric based on the motion threshold and the images, and reconstructing a final image based on the motion metric. An effective view-weighting function may be generated based on the motion metric. Another method for reducing motion artifacts includes selecting a final image from the at least two images based on the motion metric instead of reconstructing a final image, since one of the at least two images may have been reconstructed with the desired view-weighting function and additional reconstruction is redundant.

FIG. 5 shows a high-level flow chart illustrating an example method 500 for calculating a motion threshold according to an embodiment. Method 500 may comprise a subroutine of method 400 described herein above with regard to FIG. 4. Specifically, method 500 may comprise the action 415 of calculating a motion threshold. Therefore, method 500 accepts the at least two images (e.g., an un-weighted image and the at least one weighted image) reconstructed at 410 as inputs, and outputs a motion threshold calculated based on the images. Method 500 will be described with reference to the components and systems of FIGS. 1-2, as well as with reference to the method of FIG. 4, though it should be understood that the method may be applied to other components, systems, and methods without departing from the scope of the disclosure.

In the case that significant motion occurred during a scan acquisition, the images reconstructed from the acquired projection data with no view weighting will have detectable intensity differences from images reconstructed from the same projection data with a view-weighting function. Therefore, large differences between the two images may be attributed to motion during the scan acquisition. However, differences in spatial locality of motion artifacts differentially affects the ability of the image to be viewed in a clinical setting. As described herein, in order to detect the motion artifacts of clinical significance, the method considers large differences in areas of the images corresponding to regions of soft tissue.

Method 500 begins at 505. At 505, method 500 includes generating a difference image based on a difference between the two images reconstructed with different view-weighting functions. For example, the difference image may comprise the difference between the un-weighted image and the weighted image. In examples including a plurality of view-weighted images, a difference image is generated for each weighted image.

At 510, method 500 optionally includes generating a soft tissue mask based on the un-weighted image. A soft tissue mask comprises a binary image, wherein a value of one is assigned to regions of soft tissue and a value of zero is assigned to all other regions.

Thus, to generate a soft tissue mask, a minimum soft tissue threshold and a maximum soft tissue threshold are applied to the un-weighted image. Specifically, all pixels with a value between the minimum soft tissue threshold and the maximum soft tissue threshold are set to one, and all other pixels with values outside of the threshold range are set to zero.

The threshold range comprising values between the two thresholds may be selected to identify soft tissue. As an example, the minimum soft tissue threshold may be 0 HU while the maximum soft tissue threshold may be 100 HU. In other examples, the minimum soft tissue threshold may be a value other than 0 HU, for example the minimum soft tissue threshold may be within the range −50 HU to 50 HU, while the maximum soft tissue threshold may be within the range 50 HU to 150 HU. Furthermore, these threshold values may be adjusted to optimize performance. For example, the regions identified by the soft tissue thresholds may not include all soft tissue in the image, and so the values may be adjusted to capture as much of the soft tissue in the image as possible without including non-soft tissue in the soft tissue mask. Even if some soft tissue is excluded from the threshold range, the method described herein functions properly as long as a substantial amount of soft tissue in the image is included within the threshold range.

At 515, method 500 optionally includes generating a masked image by applying the soft tissue mask to the difference image. Since the soft tissue mask comprises a binary image, generating the masked image may comprise taking the dot product of the soft tissue mask and the difference image. In this way, the masked image includes the regions of the difference image corresponding to regions of soft tissue identified by the soft tissue mask, while non-soft tissue regions in the difference image are set to zero.

Since the difference image is the difference between the un-weighted image and the weighted image, large values in the difference image may correspond to motion. Therefore, large differences in the masked image may correspond to motion in the soft tissue regions. To identify which values in the masked image qualify as large differences, an estimate of background noise should be obtained. To that end, at 520, method 500 includes calculating an image deviation metric based on one or a combination of the at least two images. As a non-limiting example, the image deviation metric comprises the standard deviation. In some examples, other suitable metrics for measuring image deviation or noise may be used. The image deviation metric may be calculated based on the masked difference image. If the soft tissue mask is not generated and applied to the difference image, then the image deviation metric may be calculated based on the difference image.

At 525, method 500 includes calculating the motion threshold based on the image deviation metric. For example, in examples wherein the image deviation metric comprises the standard deviation, the motion threshold is proportional to the standard deviation. Calculating the motion threshold, then, may comprise multiplying the standard deviation by a predetermined value. As a non-limiting example, the motion threshold may be three times the standard deviation. By selecting a motion threshold greater than the standard deviation, motion in the soft tissue regions may be distinguished from background noise. Method 500 then returns.

FIG. 6 shows a high-level flow chart illustrating an example method 600 for calculating a motion metric according to an embodiment. Method 600 may comprise a subroutine of method 400 described herein above with regard to FIG. 4. Specifically, method 600 may comprise the action 420 of calculating a motion metric. Method 600 will therefore be described with reference to the components and systems of FIGS. 1-2 as well as with reference to the methods of FIGS. 4-5, though it should be understood that the method may be applied to other components, systems, and methods without departing from the scope of the disclosure.

Method 600 begins at 605. At 605, method 600 includes generating a large difference image by thresholding the masked difference image with the motion threshold. In examples wherein a soft tissue mask is not generated and applied, the large difference image may be generated by thresholding the difference image with the motion threshold. The large difference image comprises the pixels of the masked image above the motion threshold. In other words, the large difference image comprises the large differences in the (masked) difference image.

At 610, method 600 includes counting the number of pixels in each slice of the large difference image. Specifically, counting the number of pixels in each slice of the large difference image comprises counting the number of pixels with a non-zero value, or the number of large differences, in each slice.

At 615, method 600 includes generating a percentage vector by normalizing the number of pixels in each slice. Specifically, for each slice, the number of large differences (in a slice) is divided by the total number of pixels (in said slice), thereby yielding the percentage of pixels comprising large differences. Thus, the percentage vector comprises a set of values, each value representing the percentage of large differences in for a particular slice. In other words, each value of the percentage vector comprises a percentage of the total number of pixels that exceed the motion threshold in a slice of the difference image.

At 620, method 600 includes sorting the percentage vector based on the percentage of large differences. As a non-limiting example, the percentage vector may be sorted in ascending order by value. Alternatively, the percentage vector may be sorted in descending order by value.

At 625, method 600 includes generating the motion metric based on the sorted percentage vector. For example, generating the motion metric may comprise selecting the $75^{th}$ percentile of the sorted percentage vector if the percentage vector is sorted in ascending order. Similarly, the motion metric may comprise the $25^{th}$ percentile if the percentage vector is sorted in descending order. In some examples, a percentile other than the $75^{th}$ percentile may be selected based on a desired sensitivity to motion artifacts; a lower percentile may be selected for greater sensitivity to motion artifacts, while a higher percentile may be selected for reduced sensitivity to motion artifacts.

In this way, the motion metric comprises a numerical characterization of motion occurring between the intermediate images (e.g., the un-weighted image and the weighted image). Characterizing the motion in this way is a more effective representation of motion artifacts than, say, calculating a simple mean over all slices, because the intensity of motion artifacts may not be uniform over all slices. Method 600 then returns.

Thus, a method for calculating a motion metric includes calculating the percentage of pixels in each slice of an image which exceed a motion threshold.

FIGS. 7-10 shows plots of example view-weighting functions. These plots show the weight at the center of the detector in projection space as a function of the angle. Any function that has conjugate views (i.e., views separated by 180 degrees) that sum to one are viable view-weighting functions.

Figure 7:
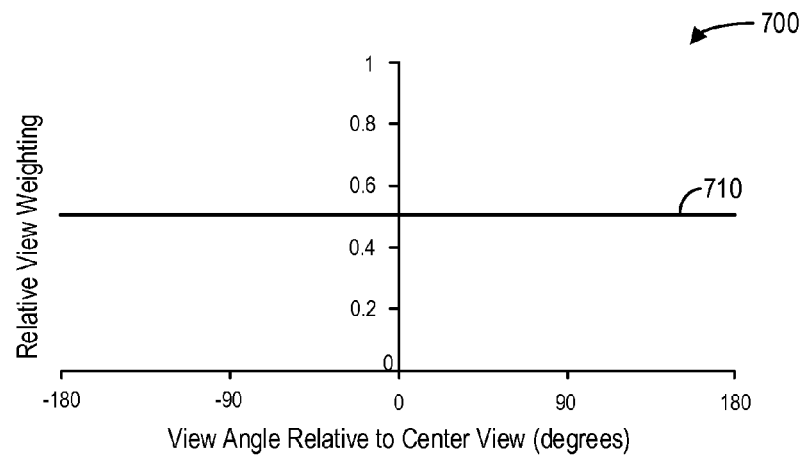
FIGS. 7-10 show plots of example view-weighting functions.

FIG. 7 shows a plot 700 of an example view-weighting function 710. In particular, the view-weighting function 710 comprises the default view-weighting function of a full scan (i.e., 360 degrees) of data. Each view has a view weight of 0.5 relative to its own conjugate view.

The view-weighting function 710 may be used to reconstruct the un-weighted images described herein above. Thus, the phrase "un-weighted image" as used herein describes an image reconstructed with the view-weighting function 710 wherein each view is equally weighted. The view-weighting functions described herein below may be used to reconstruct the weighted images described herein above.

Figure 8:
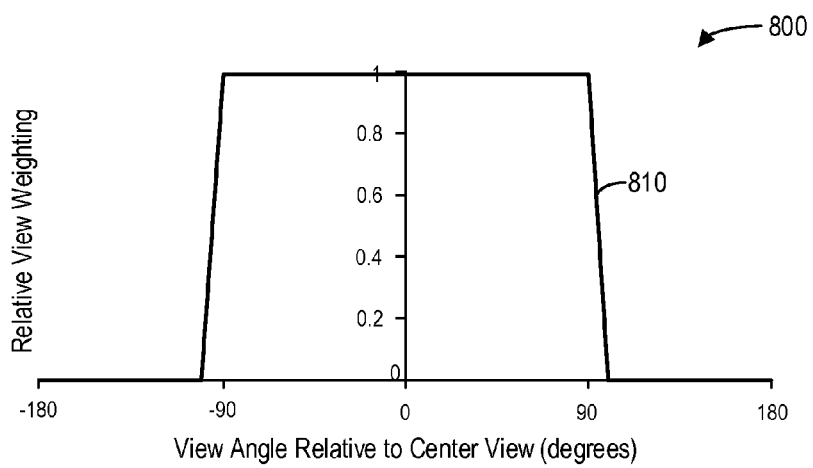

FIG. 8 shows a plot 800 of an example view weighting function 810. The view-weighting function 810 comprises the view weighting to produce a half-scan (i.e., 180 degrees plus fan angle) reconstruction from a full scan of data. Only the center views are weighted while the outer views are ignored (i.e., down weighted to zero).

Figure 9:
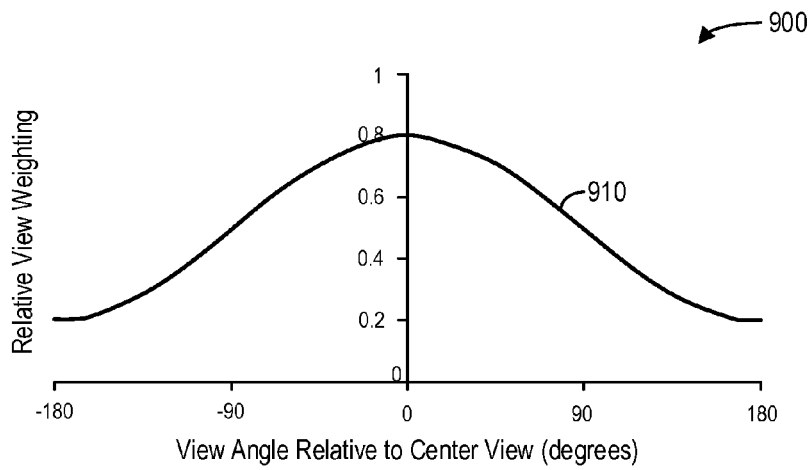

FIG. 9 shows a plot 900 of an example view-weighting function 910. The view-weighting function 910 comprises a Gaussian-like function. Furthermore, the view-weighting function 910 includes a maximum amplitude of 0.8, and so the peripheral views (i.e., the views closest to −180 and 180 degrees) are down weighted to 0.2.

Figure 10:
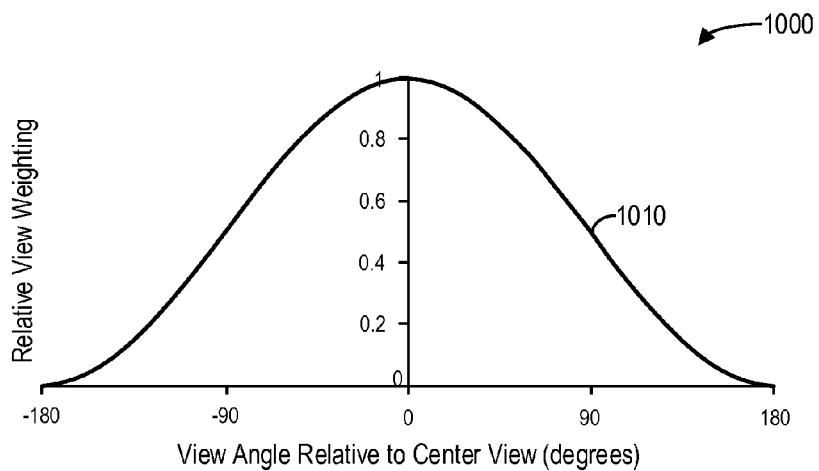

FIG. 10 shows a plot 1000 of an example view-weighting function 1010. The view-weighting function 1010 is similar to the view-weighting function 910 in that it is a Gaussian-like function. However, the view-weighting function 1010 includes a maximum amplitude of 1.0, and so the peripheral views are down weighted to zero.

Thus, a method for reducing motion artifacts in reconstructed images may include reconstructing an un-weighted image using the view-weighting function 710, and reconstructing one or more weighted images using one or more of the view-weighting functions 810, 910, and 1010. It should be appreciated that the example view-weighting functions 810, 910, and 1010 are exemplary, and that other viable view-weighting functions may improve image quality in accordance with the methods described herein. Furthermore, any new view-weighting function generated based on a motion metric is subject to the conditions described above. Specifically, the conjugate views in any new view-weighting function should sum to one.

A technical effect of the disclosure is the reduction in motion artifacts in reconstructed images. Another technical effect of the disclosure is the reconstruction of intermediate images using two or more view-weighting functions and the estimation of motion based on the intermediate images. Yet another technical effect of the disclosure is the quantitative evaluation of image quality of reconstructed images with regard to motion artifacts. Another technical effect of the disclosure is the display of an image reconstructed with a view-weighting function which down-weights slices containing motion artifacts.

In one embodiment, a method comprises reconstructing at least two images from projection data, calculating a motion metric based on the at least two images, selecting a view-weighting function based on the motion metric, and generating a display from the projection data based on the selected view-weighting function.

The method further comprises outputting the display to a display device. For example, an image reconstructed from the projection data with the view-weighting function may be output to a display. In one example, the display generated from the projection data based on the selected view-weighting function comprises one of the at least two images.

In one example, at most one of the at least two images is reconstructed based on the selected view-weighting function.

As another example, the motion metric is calculated based on a difference between the at least two images. In yet another example, the motion metric is calculated based on a normalized difference between the at least two images.

In another example, the method further comprises discarding at least one image of the at least two images reconstructed from the projection data with a view-weighting function different than the selected view-weighting function. In this way, intermediate images not selected for display can be deleted from memory and thus memory consumption may be reduced.

In one example, at most one of the at least two images is reconstructed with all of the projection data and equal weights for each view. As another example, the at least two images are reconstructed with a same center view and different view weightings. In another example, the at least two images are reconstructed with a same view weighting and different center views.

In yet another example, one image of the at least two images is reconstructed with a first view-weighting function and another image of the at least two images is reconstructed with a second view-weighting function, and selecting the view-weighting function based on the motion metric comprises selecting the first view-weighting function responsive to the motion metric above a threshold, and selecting the second view-weighting function responsive to the motion metric below the threshold.

In another embodiment, a method comprises reconstructing a first image and a second image from projection data, the first image reconstructed with a first view-weighting function and the second image reconstructed with a second view-weighting function; calculating a motion threshold based on the first image and the second image; calculating a motion metric based on the motion threshold; and generating a final reconstructed image based on the motion metric.

In one example, calculating the motion threshold comprises: generating a difference image comprising a difference between the first image and the second image; generating a soft tissue mask based on the first image; applying the soft tissue mask to the difference image to generate a masked image; calculating a standard deviation of the masked image; and calculating the motion threshold based on the standard deviation.

In another example, calculating the motion metric comprises: calculating a percentage of pixels in each slice of the masked image above the motion threshold; sorting the percentage of pixels in each slice; calculating the motion metric based on a specified percentile in the sorted percentages.

In yet another example, the method further comprises selecting a view-weighting function based on the motion metric. Selecting the view-weighting function based on the motion metric comprises: responsive to the motion metric above a threshold, selecting the second view-weighting function for final image reconstruction; and responsive to the motion metric below the threshold, selecting the first view-weighting function for the final image reconstruction. In this example, generating the final reconstructed image comprises reconstructing a final image with the selected view-weighting function and outputting the final image to a display device.

In some examples, the first image comprises a full-scan image and the second image comprises a half-scan image.

In yet another embodiment, a system comprises: an x-ray source that emits a beam of x-rays toward an object to be imaged; a detector that receives the x-rays attenuated by the object; and a data acquisition system (DAS) operably connected to the detector. The system further comprises a computer operably connected to the DAS and configured with instructions in non-transitory memory that when executed cause the computer to: reconstruct at least two images from projection data received from the DAS, each of the at least two images reconstructed with a different view-weighting function; calculate a motion metric based on the at least two images, the motion metric comprising a quantitative estimate of motion between the at least two images; generate a view-weighting function based on the motion metric; and output an image reconstructed with the generated view-weighting function.

In one example, the image reconstructed with the generated view-weighting function comprises one of the at least two images.

As another example, the generated view-weighting function comprises one of the different view-weighting functions used to reconstruct the at least two images.

In one example, at least one of the at least two images comprises a half-scan image. In another example, at most one of the at least two images comprises a full-scan image.

In one example, the system further comprises a display device, and outputting the image reconstructed with the identified view-weighting function comprises outputting the image to the display device for display to a user. Additionally, the computer is further configured with instructions in the non-transitory memory that when executed cause the computer to discard at least one image of the at least two images not displayed via the display device.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:
1. A system, comprising:
an x-ray source that emits a beam of x-rays toward an object to be imaged;
a detector that receives the x-rays attenuated by the object;
a data acquisition system (DAS) operably connected to the detector; and a computer operably connected to the DAS and configured with instructions stored in non-transitory memory that when executed cause the computer to:
reconstruct at least two images from projection data received from the DAS during a single scan of the object, each of the at least two images reconstructed with a different view-weighting function, the at least two images including a same centerview;
calculate a motion metric based on the at least two images, the motion metric comprising a quantitative estimate of motion between the at least two images;
identify a view-weighting function based on the motion metric; and
output an image reconstructed with the identified view-weighting function.

2. The system of claim 1, wherein the image reconstructed with the identified view-weighting function comprises one of the at least two images.

3. The system of claim 1, wherein the identified view-weighting function comprises one of a first and a second view-weighting function.

4. The system of claim 1, wherein at least one of the at least two images comprises a half-scan image and at most one of the at least two images comprises a full-scan image.

5. The system of claim 1, wherein identifying the view-weighting function based on the motion metric comprises generating the view-weighting function.

6. The system of claim 1, further comprising a display device, wherein outputting the image reconstructed with the identified view-weighting function comprises outputting the image to the display device for display to a user, and wherein the computer is further configured with instructions in the non-transitory memory that when executed cause the computer to discard at least one image of the at least two images not displayed via the display device.

7. A method, comprising:
reconstructing at least two images from projection data acquired during a single scan, the at least two images including a same centerview;
calculating a motion metric based on the at least two images;
selecting a view-weighting function based on the motion metric; and
generating a display from the projection data based on the selected view-weighting function.

8. The method of claim 7, wherein at most one of the at least two images is reconstructed based on the selected view-weighting function.

9. The method of claim 7, wherein the motion metric is calculated based on a difference between the at least two images.

10. The method of claim 7, wherein the motion metric is calculated based on a normalized difference between the at least two images.

11. The method of claim 7, further comprising outputting the display to a display device.

12. The method of claim 7, wherein the display generated from the projection data based on the selected view-weighting function comprises one of the at least two images.

13. The method of claim 7, further comprising discarding at least one image of the at least two images reconstructed from the projection data with a view-weighting function different than the selected view-weighting function.

14. The method of claim 7, wherein one image of the at least two images is reconstructed with a first view-weighting function and another image of the at least two images is reconstructed with a second view-weighting function, and wherein selecting the view-weighting function based on the motion metric comprises selecting the first view-weighting function responsive to the motion metric above a threshold, and selecting the second view-weighting function responsive to the motion metric below the threshold.

15. A method, comprising:
reconstructing at least a first image and a second image from projection data, the first image reconstructed with a first view-weighting function and the second image reconstructed with a second view-weighting function different from the first view-weighting function;
calculating a motion threshold based on the first image and the second image;
calculating a motion metric based on a number of pixels that exceed the motion threshold in a slice of an image; and
generating a final reconstructed image based on the motion metric.

16. The method of claim 15, wherein calculating the motion threshold comprises:
generating a difference image comprising a difference between the first image and the second image;
generating a soft tissue mask based on the first image;
applying the soft tissue mask to the difference image to generate a masked image;
calculating a standard deviation of the masked image; and
calculating the motion threshold based on the standard deviation.

17. The method of claim 16, wherein calculating the motion metric comprises:
calculating a percentage of pixels in each slice of the masked image above the motion threshold;
sorting the percentage of pixels in each slice; and
calculating the motion metric based on a specified percentile in the sorted percentages.

18. The method of claim 15, further comprising selecting a view-weighting function based on the motion metric, wherein selecting the view-weighting function based on the motion metric comprises:
responsive to the motion metric above a threshold, selecting the second view-weighting function for final image reconstruction; and
responsive to the motion metric below the threshold, selecting the first view-weighting function for the final image reconstruction.

19. The method of claim 18, wherein generating the final reconstructed image comprises reconstructing a final image with the selected view-weighting function and outputting the final image to a display device.

20. The method of claim 15, wherein the first image comprises a full-scan image and the second image comprises a half-scan image.

* * * * *